United States Patent
Farrand et al.

(10) Patent No.: US 7,943,061 B2
(45) Date of Patent: May 17, 2011

(54) CHIRAL BINAPHTHYL SULFATES FOR USE AS LIQUID CRYSTAL MATERIALS

(75) Inventors: Louise Diane Farrand, Poole (GB); Patricia Eileen Saxton, Hampshire (GB)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 15 days.

(21) Appl. No.: 12/296,598

(22) PCT Filed: Mar. 16, 2007

(86) PCT No.: PCT/EP2007/002333
§ 371 (c)(1), (2), (4) Date: Jul. 23, 2009

(87) PCT Pub. No.: WO2007/115639
PCT Pub. Date: Oct. 18, 2007

(65) Prior Publication Data
US 2010/0019199 A1    Jan. 28, 2010

(30) Foreign Application Priority Data
Apr. 10, 2006  (EP) ................................ 06007493

(51) Int. Cl.
*C09K 19/00* (2006.01)
*C09K 19/06* (2006.01)
*C09K 19/52* (2006.01)

(52) U.S. Cl. ........... 252/299.01; 252/299.6; 252/299.61; 252/299.62; 252/299.63; 428/1.1; 430/20; 349/167; 349/182

(58) Field of Classification Search ............. 252/299.01, 252/299.6–299.67; 428/1.1; 430/20; 349/167, 349/182
See application file for complete search history.

(56) References Cited

U.S. PATENT DOCUMENTS

2003/0006398 A1   1/2003   Yumoto et al.
2005/0179005 A1   8/2005   Kato et al.

FOREIGN PATENT DOCUMENTS

WO            0234739 A1      5/2002

*Primary Examiner* — Geraldina Visconti
(74) *Attorney, Agent, or Firm* — Millen, White, Zelano & Branigan, P.C.

(57) ABSTRACT

The invention relates to chiral compounds, methods of their preparation, and to their use in optical, electrooptical, electronic, semiconducting or luminescent components or devices, and in decorative, security, cosmetic or diagnostic applications.

11 Claims, No Drawings

CHIRAL BINAPHTHYL SULFATES FOR USE AS LIQUID CRYSTAL MATERIALS

FIELD OF THE INVENTION

The invention relates to chiral compounds, methods of their preparation, and to their use in optical, electrooptical, electronic, semiconducting or luminescent components or devices, and in decorative, security, cosmetic or diagnostic applications.

BACKGROUND AND PRIOR ART

Chiral liquid crystal (LC) materials are useful for many applications, for example LC displays (LCD) or polymer films with a twisted structure. Usually they consist of an LC host material containing one or more chiral dopants which induce the desired helical twist. The effectiveness of a chiral compound to induce a helically twisted molecular structure in a liquid crystal host material is described by its so-called helical twisting power (HTP). The HTP is given in first approximation, which is sufficient for most practical applications, by equation (1):

$$HTP = \frac{1}{p \cdot c} \qquad (1)$$

wherein c is the concentration of the chiral compound in the host material and p is the helical pitch.

As can be seen from equation (1), a short pitch can be achieved by using a high amount of the chiral compound or by using a chiral compound with a high absolute value of the HTP. Thus, in case chiral compounds with low HTP are used, high amounts are needed to induce a short pitch. This can be disadvantageous in case the chiral dopant has a negative influence on the properties of the LC host mixture, like clearing point, dielectric anisotropy, viscosity, driving voltage or switching times. Also, chiral dopants are typically used as pure enantiomers and can be expensive and difficult to synthesize.

A cheap, stable, chiral polymerisable dopant is an essential component for the mass production of cholesteric and other chiral optical polymer films made from reactive mesogens for display applications. A chiral dopant is also required for example in the mass production of security films made from reactive mesogens, and in LCD applications, like for example LCDs utilising the electro-optical blue phase as a switching medium, or surface-stabilised cholesteric texture (SSCT) displays.

However, many of the chiral dopants described in prior art are expensive because of the cost of the starting materials or the number of steps required for production of the final compound. In addition, many chiral dopants described in prior art do not have a very high twisting power (i.e. a high absolute value of the HTP), meaning that a large amount of the dopant is required to achieve an appropriate level of helicity and selective Bragg reflection, as shown above. This makes the LC material expensive.

Also, chiral dopants known from prior art often show low solubility in the LC host material, which leads to undesired crystallization at low temperatures. To overcome this disadvantage, typically two or more different chiral dopants have to be added to the host mixture. This implies higher costs and usually also requires additional effort for temperature compensation of the material, since the different dopants have to be selected such that their temperature coefficients of the twist will compensate each other.

Consequently, there is a considerable demand for chiral compounds which have a high twisting power, are easy to manufacture, can be used in low amounts, show low temperature dependence of the twisting power e.g. for utilizing a constant reflection wavelength, show good solubility in an LC host material and do not have a negative influence on the properties of the LC host.

The invention has the aim of providing chiral compounds having these properties, and not having the above-mentioned disadvantages of prior art chiral compounds. Another aim of the invention is to extend the pool of chiral compounds available to the expert. Other aims are immediately evident to the expert from the following description.

The inventors of the present invention have found that these aims can be achieved by providing chiral compounds as claimed in this invention, which are derived from substituted 1,1'-binaphthyl-2,2'-diyl sulfate.

1,1'-Binaphthyl-2,2'-diyl sulfate is disclosed in C. Koy et al., Sulfur Letters 1998, 21(2), 75-88. However, substituted binaphthyl sulfates as claimed in the present invention are not disclosed.

SUMMARY OF THE INVENTION

The invention relates to compounds of formula I

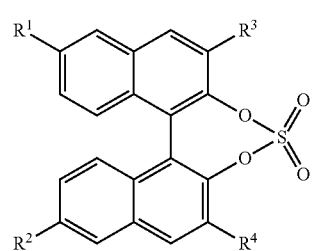

wherein
$R^{1-4}$ independently of each other denote H, F, Cl, Br, I, CN, NCS, $SF_5$, or straight-chain, branched or cyclic alkyl, aryl or heteroaryl having 1 to 30 C-atoms that is optionally mono- or polysubstituted by F, Cl, Br, I or CN, and in which one or more non-adjacent $CH_2$ groups are optionally replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote -(Z$^1$-A$^1$)$_m$—R$^5$ or P-Sp-,
$R^5$ has one of the meanings of $R^1$ that is different from -(Z$^1$-A$^1$)$_m$—R$^5$,
P is a polymerisable group,
Sp is a spacer group or a single bond,
$A^1$ is, in case of multiple occurrence independently of one another, an aromatic or alicyclic group, which optionally contains one or more heteroatoms selected from N, O and S, and is optionally mono- or polysubstituted by $R^1$,
$Z^1$ in case of multiple occurrence independently of one another denotes —O—, —S—, —CO—, —COO—, —OCO—, —S—CO—, —CO—S—, —O—COO—, —CO—NR$^o$—, —NR$^o$—CO—, —NR$^o$—CO—NR$^{oo}$, —NR$^o$—CO—O—, —O—CO—NR$^o$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —$(CH_2)_4$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—COO—, —OCO—CH=CH— or a single bond, $R^0$ and $R^{00}$ independently of each other denote H or alkyl with 1 to 12 C-atoms, $Y^1$ and $Y^2$ independently of each other denote H, F, Cl or CN, m is 0, 1, 2, 3 or 4, wherein the binaphthyl group is optionally substituted in further positions by one or more identical or different groups $R^1$, and wherein the compound comprises at least one substituent $R^{1-4}$ that is different from H.

The invention further relates to methods of preparing a compound of formula I and to novel intermediates used therein.

The invention further relates to an LC material comprising one or more compounds of formula I.

The invention further relates to a chiral anisotropic polymer obtained by polymerising a compound of formula I or an LC material as described above and below, preferably in its oriented state in form of a thin film.

The invention further relates to the use of compounds, materials and polymers as described above and below in electrooptical displays, LCDs, optical films, polarisers, compensators, beam splitters, reflective films, alignment layers, colour filters, holographic elements, hot stamping foils, coloured images, decorative or security markings, LC pigments, adhesives, cosmetics, diagnostics, non-linear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, or as chiral dopants.

TERMS AND DEFINITIONS

The term "film" includes rigid or flexible, self-supporting or free-standing films with mechanical stability, as well as coatings or layers on a supporting substrate or between two substrates.

The term "liquid crystal or mesogenic material" or "liquid crystal or mesogenic compound" means materials or compounds comprising one or more rod- or board-shaped (calamitic) or disk-shaped (discotic) mesogenic groups, i.e. groups with the ability to induce liquid crystal (LC) phase behaviour. The compounds or materials comprising mesogenic groups do not necessarily have to exhibit an LC phase themselves. It is also possible that they show LC phase behaviour only in mixtures with other compounds, or when the mesogenic compounds or materials, or the mixtures thereof, are polymerised.

For the sake of simplicity, the term "liquid crystal material" is used hereinafter for both mesogenic and LC materials.

Polymerisable compounds with one polymerisable group are also referred to as "monoreactive" compounds, compounds with two polymerisable groups as "direactive" compounds, and compounds with more than two polymerisable groups as "multireactive" compounds. Compounds without a polymerisable group are also referred to as "non-reactive" compounds.

The term "reactive mesogen" (RM) means a polymerisable mesogenic or liquid crystal compound.

The compounds of formula I as described above and below are chiral and can be used as pure S,S- and R,R-isomers or as mixture thereof or as a racemic mixture thereof (racemate). Especially preferred are the enantiomerically pure compounds, furthermore the racemate. Unless stated otherwise, the formulae, subformulae and other disclosure relating to binaphthyls of formula I above and below include both the S,S- and R,R-isomers and their racemic mixture.

DETAILED DESCRIPTION OF THE INVENTION

The compounds of formula I can be used to make optical films, in particular optical retardation or compensation films, alignment layers or polarisers for LCDs, especially if they have a polymerisable group. They can also be useful in applications which do not require a polymerisable group, for example as dopant in SSCT or electro-optical blue phase LCDs.

The compounds of formula I themselves do not have to exhibit an LC phase. However, as they are partially consisting of a rod like structure they do not diminish the electro-optical properties of the LC host in to which they are dissolved, for example clearing points are not significantly lowered.

The compounds of formula I are highly polar. Therefore they are useful for achieving polymer films with high adhesion. In addition, they have very good solubility in polar LC mixtures compared to less polar dopants In contrast, almost all chiral dopants hitherto known from in prior art are dielectrically neutral.

In addition, the compounds of formula I have the following advantages they can be prepared from cheap, readily available starting materials in a few manufacturing steps in good yield, also on large scale of several hundred grams, with a broad range of derivatives using standard methods that are known from the literature, the starting materials can be obtained commercially, they can be prepared enantiomerically pure as compounds of different handedness (left handed and right handed), enabling both left and right handed helices to be formed in a nematic host, which is particularly useful for security film applications, they exhibit a high HTP.

Especially preferred are compounds of formula I, wherein
$R^1$ and $R^2$ are identical groups,
$R^3$ and $R^4$ are identical groups,
$R^1$ and/or $R^2$ is different from H,
$R^3$ and/or $R^4$ is different from H,
$R^1$ and/or $R^2$ are P-Sp-,
$R^3$ and/or $R^4$ are P-Sp-,
P-Sp- is P—$(CH_2)_a$—$(O)_b$— with a being an integer from 1 to 12, preferably 1 to 6, and b being 0 or 1,
one or more of $R^{1-4}$ are selected from identical or different alkyl or alkoxy with 1 to 12 C atoms that is optionally fluorinated,
the compounds comprise at least one group $R^{1-4}$ or $R^5$ that is P-Sp-,
$R^1$ and/or $R^2$ denote -$(Z^1$-$A^1)_m$—$R^5$, with $R^5$, $Z^1$, $A^1$ and m being as defined above,
$R^3$ and/or $R^4$ denote -$(Z^1$-$A^1)_m$-$R^5$, with $R^5$, $Z^1$, $A^1$ and m being as defined above,
$R^5$ is P-Sp-,
$R^5$ is alkyl or alkoxy with 1 to 12 C atoms that is optionally fluorinated,
m is 1, 2 or 3,
at least one of the groups $Z^1$, preferably the one linked to the binaphthol group, is —C≡C—,
at least one of the groups $Z^1$, preferably the one linked to the binaphthol group, is a single bond.

Preferred cycloalkyl, aryl and heteroaryl groups include, without limitation, furan, pyrrol, thiophene, oxazole, thiazole, thiadiazole, imidazole, phenylene, cyclohexylene, bicyclooctylene, cyclohexenylene, pyridine, pyrimidine, pyrazine, azulene, indane, naphthalene, tetrahydronaphthalene, anthracene and phenanthrene, all of which are optionally substituted by one or more groups L, with L having one of the meanings of $R^1$ given in formula I.

Particular preferred cycloalkyl, aryl and heteroaryl groups are selected from 1,4-phenylene, pyridine-2,5-diyl, pyrimidine-2,5-diyl, thiophene-2,5-diyl, naphthalene-2,6-diyl, 1,2,3,4-tetrahydro-naphthalene-2,6-diyl, indane-2,5-diyl, bicyclooctylene or 1,4-cyclohexylene wherein one or two non-adjacent $CH_2$ groups are optionally replaced by O and/or S, wherein these groups are unsubstituted, mono- or polysubstituted by L as defined above.

Preferably L is selected from F, Cl, Br, I, —CN, —$NO_2$, —NCO, —NCS, —OCN, —SCN, —C(=O)$NR^0R^{00}$, —C(=O)$OR^0$, —C(=O)$R^0$, —C(=O)X, —$NR^0R^{00}$, —OH, —$SF_5$, optionally substituted silyl, aryl with 1 to 12, preferably 1 to 6 C atoms, and straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl, wherein $R^0$ and $R^{00}$ are as defined above and X is halogen.

More preferably L is selected from F, Cl, CN, $NO_2$ or straight chain or branched alkyl, alkoxy, alkylcarbonyl, alkoxycarbonyl, alkylcarbonyloxy or alkoxycarbonyloxy with 1 to 12 C atoms, wherein the alkyl groups are optionally perfluorinated.

Most preferably L is selected from F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$ or $OC_2F_5$, in particular F, Cl, CN, $CH_3$, $C_2H_5$, $C(CH_3)_3$, $CH(CH_3)_2$, $OCH_3$, $COCH_3$ or $OCF_3$, most preferably F, Cl, $CH_3$, $C(CH_3)_3$, $OCH_3$ or $COCH_3$.

Some preferred groups -$(Z^1-A^1)_m$- are listed below. For reasons of simplicity, Phe in these groups is 1,4-phenylene, PheL is 1,4-phenylene that is substituted with 1 to 4 groups L as defined in formula I, Cyc is 1,4-cyclohexylene and Z has one of the meanings of $Z^1$ in formula I. The list is comprising the following subformulae as well as their mirror images -PheL-   II-1

-PheL-Z-Phe-   II-2

-PheL-Z-PheL-   II-3

-Phe-Z-Cyc-   II-4

-PheL-Z-Cyc-   II-5

Z is preferably —O—, —COO—, —OCO—, —CH=CH—, —C≡C—, —CH=CH—COO—, —OCO—CH=CH—, —$CH_2CH_2$— or a single bond.

Very preferably the group -$(Z^1-A^1)_m$- is selected from the following formulae and their mirror images, wherein Z denotes the linkage to the binaphthol group

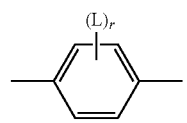
IIa

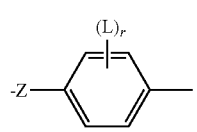
IIb

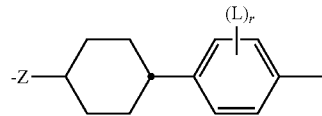
IIc

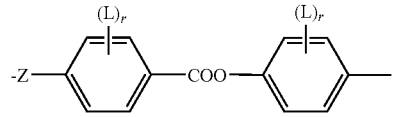
IId

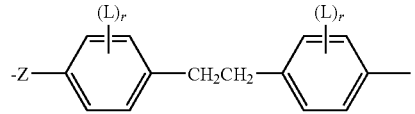
IIe

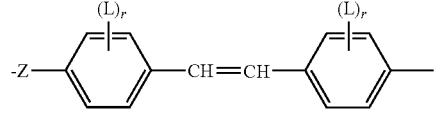
IIf

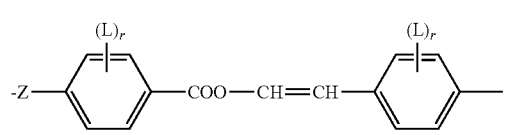
IIg

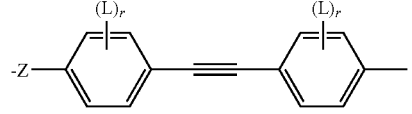
IIh

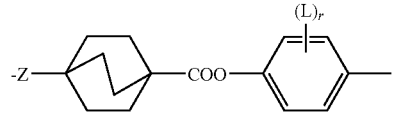
IIi

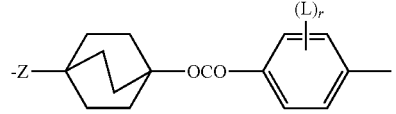
IIk wherein L and Z are as defined above, Z is especially preferably —C≡C— or a single bond, and r is 0, 1, 2, 3 or 4, preferably 0, 1 or 2.

A group

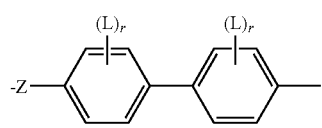

wherein r is different from 0 is preferably denoting

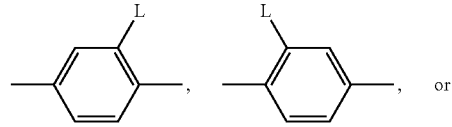

-continued

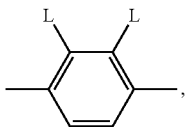

furthermore

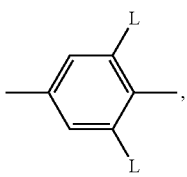

with L having each independently one of the meanings given above.

Very preferred compounds of formula I comprise at least two groups

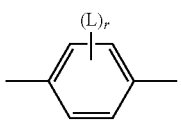

wherein r is 1 or at least one group

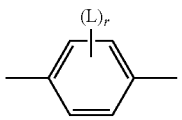

wherein r is 2.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

An alkyl group wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

In an alkyl group wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

An alkyl or alkenyl group that is monosubstituted by CN or $CF_3$ is preferably straight-chain. The substitution by CN or $CF_3$ can be in any desired position.

An alkyl or alkenyl group that is at least monosubstituted by halogen is preferably straight-chain. Halogen is preferably F or Cl, in case of multiple substitution preferably F. The resulting groups include also perfluorinated groups. In case of monosubstitution the F or Cl substituent can be in any desired position, but is preferably in ω-position. Examples for especially preferred straight-chain groups with a terminal F substituent are fluoromethyl, 2-fluorethyl, 3-fluorpropyl, 4-fluorbutyl, 5-fluorpentyl, 6-fluorhexyl and 7-fluorheptyl. Other positions of F are, however, not excluded.

Halogen is preferably F or Cl.

The polymerisable group P is a group that is capable of participating in a polymerisation reaction, like radical or ionic chain polymerisation, polyaddition or polycondensation, or capable of being grafted, for example by condensation or addition, to a polymer backbone in a polymer analogous reaction. Especially preferred are polymerisable groups for chain polymerisation reactions, like radical, cationic or anionic polymerisation. Very preferred are polymerisable groups comprising a C—C double or triple bond, and polymerisable groups capable of polymerisation by a ring-opening reaction, like oxetanes or epoxides.

Very preferably the polymerisable group P is selected from $CH_2=CW^1$-COO—, $CH_2=CW^1$—CO—,

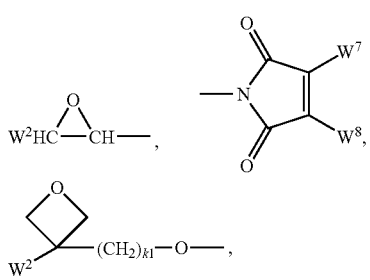

$CH_2=CW^2-(O)_{k1}-$, $CH_3-CH=CH-O-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}$-Phe-$(O)_{k2}-$, $CH_2=CH-(CO)_{k1}$-Phe-$(O)_{k2}-$, Phe-CH=CH—, HOOC—, OCN—, and $W^4W^5W^6Si-$, with $W^1$ being H, F, Cl, CN, $CF_3$, phenyl or alkyl with 1 to 5 C-atoms, in particular H, $C_1$ or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Especially preferred groups P are $CH_2=CH-COO-$, $CH_2=C(CH_3)-COO-$, $CH_2=CH-$, $CH_2=CH-O-$, $(CH_2=CH)_2CH-OCO-$, $(CH_2=CH)_2CH-O-$,

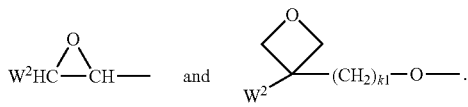

Especially preferably Pg is a vinyl group, an acrylate group, a methacrylate group, an oxetane group or an epoxy group, especially preferably an acrylate or methacrylate group.

Very preferred are acrylate and oxetane groups. Oxetanes produce less shrinkage upon polymerisation (cross-linking), which results in less stress development within films, leading to higher retention of ordering and fewer defects. Oxetane cross-linking also requires a cationic initiator, which unlike a free radical initiator is inert to oxygen.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'-, wherein Sp' is alkylene with 1 to 20 C atoms, preferably 1 to 12 C-atoms, which is optionally mono- or polysubstituted by F, Cl, Br, I or CN, and wherein one or more non-adjacent $CH_2$ groups are optionally replaced, in each case independently from one another, by —O—, —S—, —NH—, $—NR^o—$, $—SiR^oR^{oo}—$, —CO—, —COO—, —OCO—, —OCO—O—, —S—CO—, —CO—S—, $—NR^o—CO—O—$, $—O—CO—NR^o—$, $—NR^o—CO—NR^o—$, —CH=CH— or —C≡C— in such a manner that O and/or S atoms are not linked directly to one another, X' is —O—, —S—, —CO—, —COO—, —OCO—, —O—COO—, $—CO—NR^o—$, $—NR^o—CO—$, $—NR^o—CO—NR^o—$, $—OCH_2—$, $—CH_2O—$, $—SCH_2—$, $—CH_2S—$, $—CF_2O—$, $—OCF_2—$, $—CF_2S—$, $—SCF_2—$, $—CF_2CH_2—$, $—CH_2CF_2—$, $—CF_2CF_2—$, —CH=N—, —N=CH—, —N=N—, $—CH=CR^o—$, $—CY^1=CY^2—$, —C≡C—, —CH=CH—COO—, —OCO—CH=CH— or a single bond, $R^o$ and $R^{oo}$ are independently of each other H or alkyl with 1 to 12 C-atoms, and $Y^1$ and $Y^2$ are independently of each other H, F, Cl or CN.

X' is preferably —O—, —S—CO—, —COO—, —OCO—, —O—COO—, $—CO—NR^o—$, $—NR^o—CO—$, $—NR^o—CO—NR^o—$ or a single bond.

Typical groups Sp' are, for example, $—(CH_2)_p—$, $—(CH_2CH_2O)_q—CH_2CH_2—$, $—CH_2CH_2—S—CH_2CH_2—$ or $—CH_2CH_2—NH—CH_2CH_2—$ or $—(SiR^oR^{oo}—O)_p—$, with p being an integer from 2 to 12, q being an integer from 1 to 3 and $R^o$ and $R^{oo}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxy-butylene, ethylene-thioethylene, ethylene-N-methyl-iminoethylene, 1-methylalkylene, ethenylene, propenylene and butenylene for example.

Further preferred are compounds with one or two groups P-Sp- wherein Sp is a single bond. In case of compounds with two groups P-Sp, each of the two polymerisable groups P and the two spacer groups Sp can be identical or different.

Particularly preferred compounds of formula I are those of the following formulae

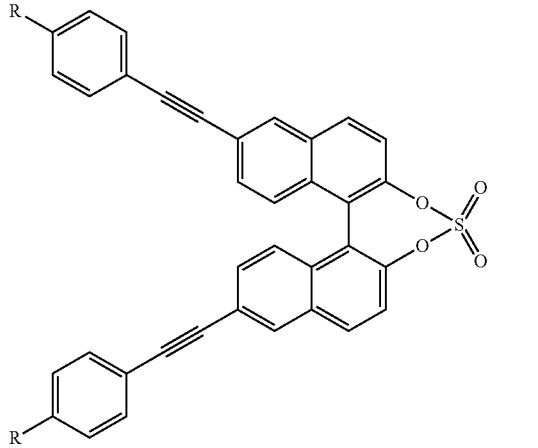

Ia

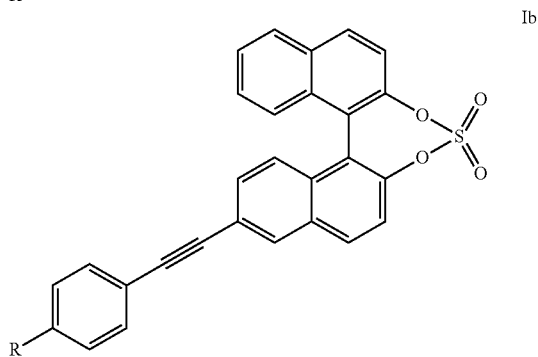

Ib

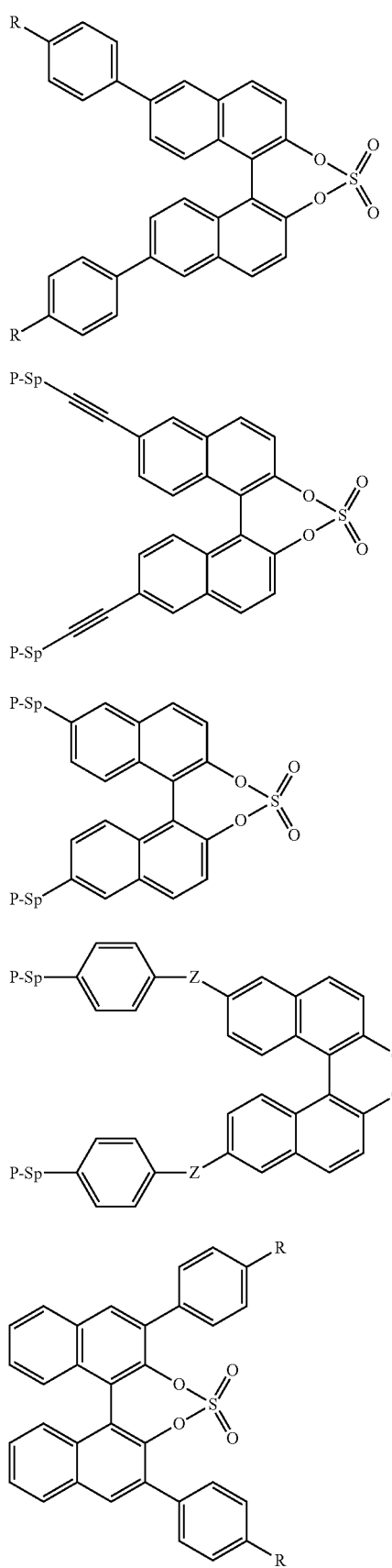
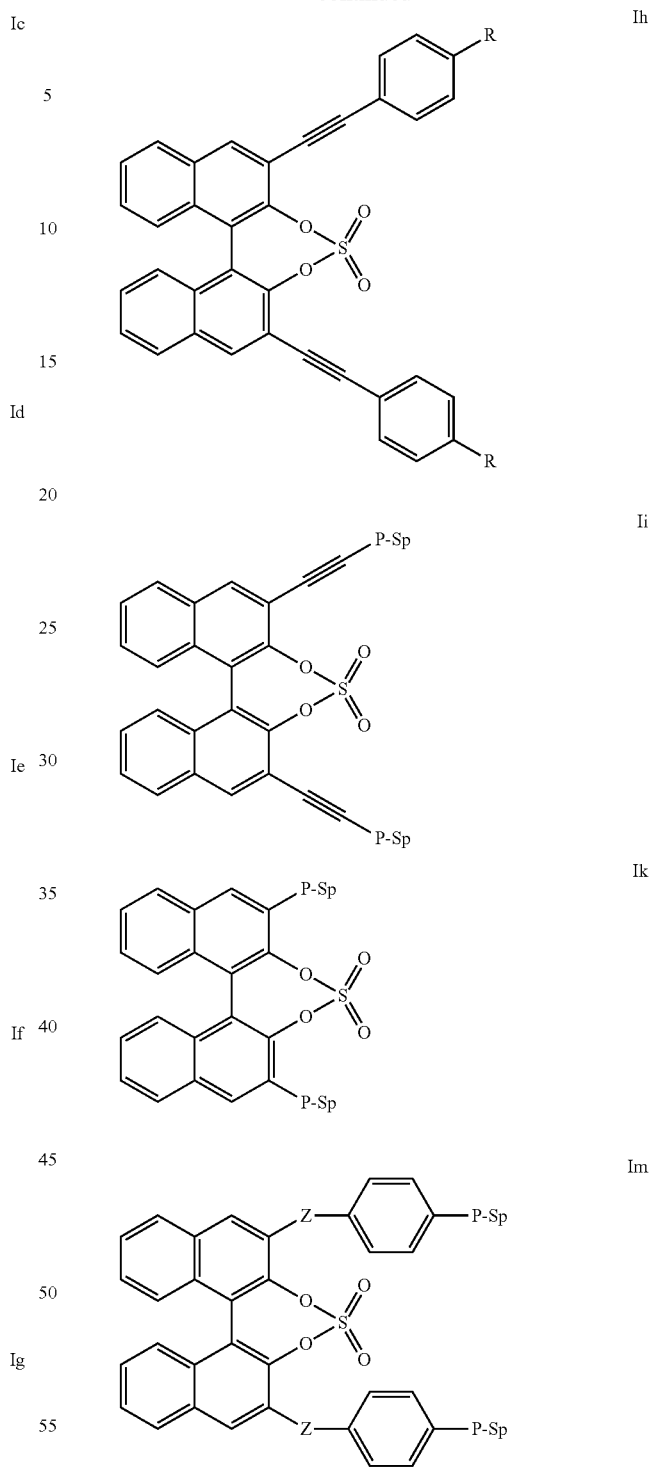
wherein P and Sp are as defined above, R has one of the meanings of $R^1$ given above, and Z has one of the meanings of $Z^1$ given above.
Especially preferred are compounds of formula Ia, Ib, Ic, Ig and Ih wherein R is alkyl or alkoxy, that is very preferably straight-chain and has 1 to 6 C-atoms.
Further preferred are compounds of formula If and Im wherein Z is —COO— or —OCO—.

Further preferred are compounds of formula Id, Ie, If, Ii, Ik and Im wherein P-Sp is CH$_2$=CW-COO—(CH$_2$)$_a$—(O)$_b$—, wherein W is H or CH$_3$ and a and b are as defined above.

The compounds of formula I can be synthesized according to or in analogy to methods which are known per se and which are described in the literature and in standard works of organic chemistry such as, for example, Houben-Weyl, Methoden der organischen Chemie, Thieme-Verlag, Stuttgart. Preferably the compounds are synthesized according or in analogy to the following methods.

Scheme 1

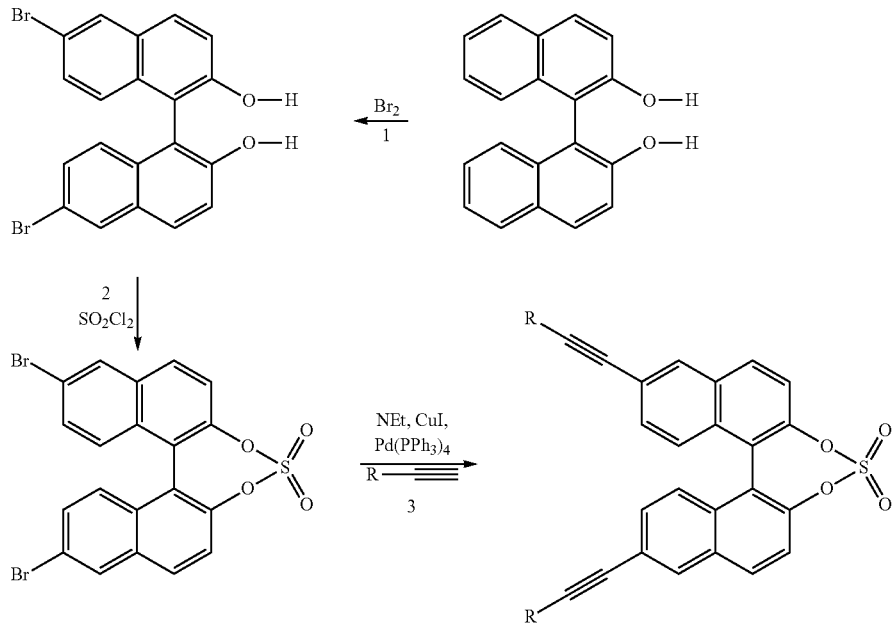

wherein R is alkyl, R-aryl, P-Sp- or P-Sp-aryl

Scheme 2

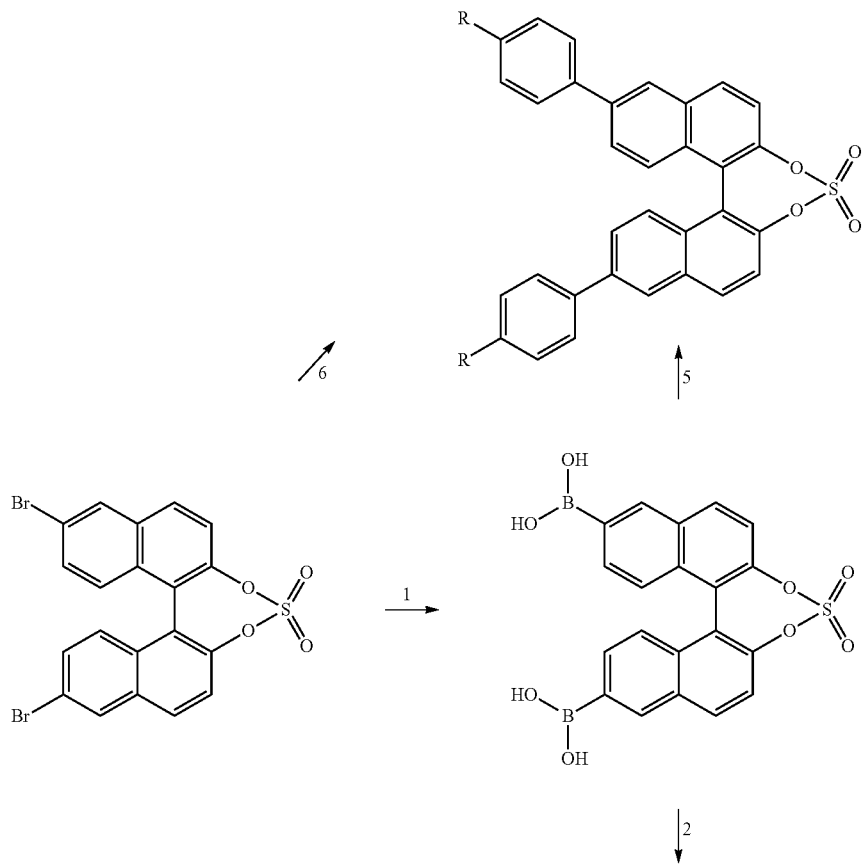

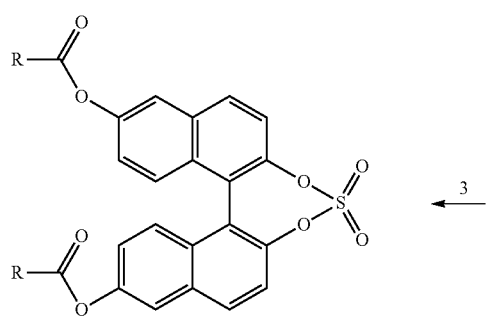

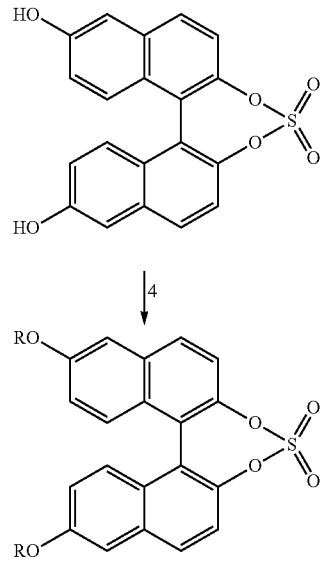

wherein R is alkyl or P.

Step 1: Grignard formation, reaction with triisopropylborate, followed by hydrolysis to give the boronic acid intermediate.
Step 2: Reaction with $H_2O_2$ to give phenol.
Step 3: Esterification by means of RCOCl, triethylamine.
Step 4: Etherification by means of RBr, $K_2CO_3$, butanone.
Step 5: Palladium C—C cross coupling under Suzuki conditions, RBr, $Pd(PPh_3)_4$.
Step 6: Palladium C—C cross coupling under Suzuki conditions, $RB(OH)_2$, $Pd(PPh_3)_4$.

The methods shown above and below and the intermediates used therein are another aspect of the present invention.

Especially preferred are the following methods and intermediates (see Schemes 1 and 2):

Method of preparing a compound of formula I by
a) reacting binaphthol with bromine,
b) reacting the intermediate 6,6'-dibromo-[1,1']binaphthalenyl-2,2'-diol with sulphuryl chloride or another sulphuric acid derivative to form a dibromobinaphthtol sulphate intermediate,
and
c1) reacting the dibromobinaphthol sulphate intermediate with an aromatic or aliphatic acetylene compound in the presence of a base, and a catalytic amount of a copper salt and a palladium catalyst to form the desired product,
or
c2) Grignard reaction of the dibromobinaphthol sulphate intermediate with a borate, followed by hydrolysis to give the boronic acid intermediate,
d2) reaction of the boronic acid intermediate with $H_2O_2$ to give a phenol,
e2) esterification of the phenol with an aliphatic or aromatic carboxylic acid derivative in the presence of a base,
or
c3) Grignard reaction of the dibromobinaphthol sulphate intermediate with a borate, followed by hydrolysis to give the boronic acid intermediate,
d3) reaction of the boronic acid intermediate with $H_2O_2$ to give a phenol,
e3) etherification of the phenol by means of an aliphatic or aromatic halogenid in the presence of a base,
or
c4) Grignard reaction of the dibromobinaphthol sulphate intermediate with a borate, followed by hydrolysis to give the boronic acid intermediate,
d4) palladium C—C cross coupling of the boronic acid intermediate with an aliphatic or aromatic halogenid under Suzuki conditions,
or
c5) palladium C—C cross coupling of the dibromobinaphthol sulphate intermediate with an aliphatic or aromatic boronic acid under Suzuki conditions.

The methods shown above and below and the intermediates used therein are another aspect of the present invention.

The compounds of formula I can be used in LC mixtures for LCDs exhibiting a twisted structure like, for example, twisted or supertwisted nematic (TN, STN) displays with multiplex or active matrix addressing, or in cholesteric displays like surface stabilized or polymer stabilized cholesteric texture displays (SSCT, PSCT) as described in WO 92/19695, WO 93/23496, U.S. Pat. Nos. 5,453,863 or 5,493,430, for LCDs with variable pitch, like multi-domain LCDs as described in WO 98/57223, multicolour cholesteric displays as described in U.S. Pat. No. 5,668,614, or displays comprising a chiral LC medium operating in the isotropic or blue phase as described in WO 02/93244. They can also be used in flexoelectric displays as described for example in GB 2 356 629.

The inventive compounds of formula I are also suitable for use in thermochromic or photochromic LC media, which change their colour upon temperature change or photoirradiation, respectively.

Thus, another aspect of the invention is an LC mixture comprising at least one chiral compound of formula I. Yet another aspect of the invention are cholesteric LCDs comprising cholesteric LC media containing at least one chiral compound of formula I.

The compounds of formula I have a good solubility in LC host mixtures, and can be added as dopants to LC hosts in high amounts without significantly affecting the phase behaviour and electrooptical properties of the mixture. Undesired spontaneous crystallization at low temperatures is thereby reduced and the operating temperature range of the mixture can be broadened. Furthermore, they can be used for the preparation of highly twisted LC media even if they have a low HTP, because the dopant concentration can be increased to yield low pitch values (i.e. high twist) without affecting the mixture properties. The use of a second dopant, which is often added to avoid crystallization, can thus be avoided. As the chiral compounds of formula I exhibit high HTP values, an LC mixture with high helical twist, i.e. a low pitch, can be prepared by adding these compounds in very small amounts.

Such an LC mixture comprises preferably 0.1 to 30%, in particular 1 to 25% and very particularly preferably 2 to 15% by weight of chiral compounds of formula I. Preferably it comprises 1 to 3 chiral compounds of formula I.

In a preferred embodiment of the invention the LC mixture is consisting of 2 to 25, preferably 3 to 15 compounds, at least one of which is a chiral compound of formula I. The other compounds are preferably low molecular weight LC compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexyl-biphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclo-hexylpyrimidines, phenyl- or cyclohexylpyridines, phenyl- or cyclohexylpyridazines, phenyl- or cyclohexyldioxanes, phenyl- or cyclo-hexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated. The LC mixture is preferably based on achiral compounds of this type.

The most important compounds that can be used as components of the LC mixture can be characterized by the following formula

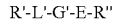

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

A preferred use of the compounds of formula I is the preparation of polymerisable LC mixtures, anisotropic polymer gels and anisotropic polymer films, in particular polymer films that exhibit a helically twisted molecular structure with uniform planar orientation, i.e. wherein the helical axis is oriented perpendicular to the plane of the film, like oriented cholesteric films.

Anisotropic polymer gels and displays comprising them are disclosed for example in DE 195 04 224 and GB 2 279 659.

Oriented cholesteric polymer films can be used for example as broadband reflective polarisers, colour filters, security markings, or for the preparation of LC pigments.

Thus, another aspect of the invention is a polymerisable LC material comprising one or more compounds of formula I and one or more further compounds, which can also be polymerisable and/or LC compounds.

The polymerisable LC material is preferably a mixture of two or more compounds, at least one of which is polymerisable or cross-linkable compound. Polymerisable compounds with one polymerisable group are hereinafter also referred to as "monoreactive". Cross-linkable compounds, i.e. having two or more polymerisable groups, are hereinafter also referred to as "di- or multireactive".

The polymerisable mesogenic or LC compounds are preferably monomers, very preferably calamitic monomers. These materials typically have good optical properties, like reduced chromaticity, and can be easily and quickly aligned into the desired orientation, which is especially important for the industrial production of polymer films at large scale. It is also possible that the polymerisable material comprises one or more discotic monomers.

The polymerisable materials as described above and below are another aspect of the invention.

Polymerisable mesogenic mono-, di- and multireactive compounds suitable for the present invention can be prepared by methods which are known per se and which are described in standard works of organic chemistry like for example Houben-Weyl, Methoden der organischen Chemie, Thieme-Verlag, Stuttgart.

Suitable polymerisable mesogenic or LC compounds for use as monomer or co-monomer in a polymerisable LC mixture are disclosed for example in WO 93/22397, EP 0 261 712, DE 195 04 224, WO 95/22586, WO 97/00600, U.S. Pat. Nos. 5,518,652, 5,750,051, 5,770,107 and 6,514,578.

Examples of suitable and preferred polymerisable mesogenic or LC compounds (reactive mesogens) are shown in the following list.

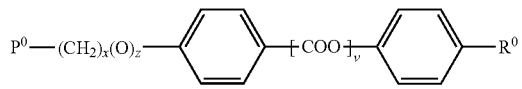
(R1)
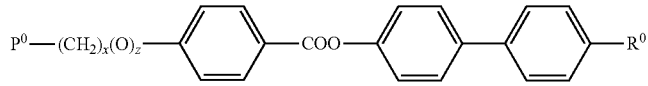
(R2)
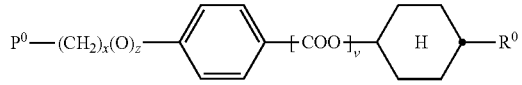
(R3)
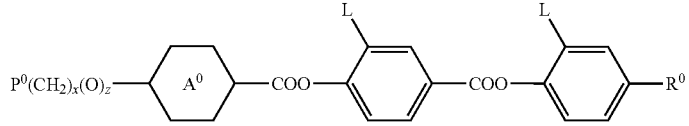
(R4)
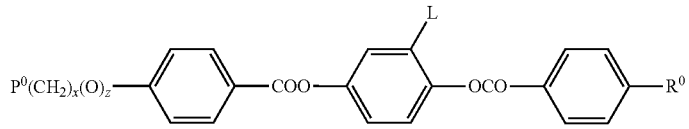
(R5)
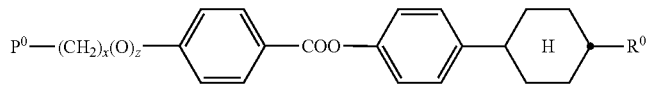
(R6)
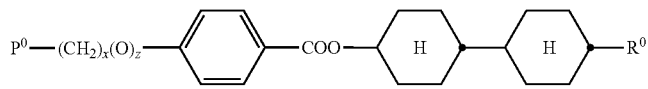
(R7)
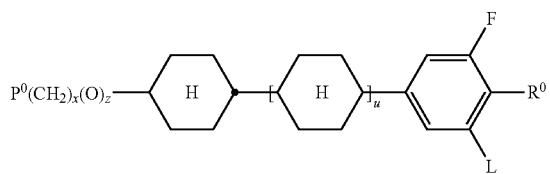
(R8)
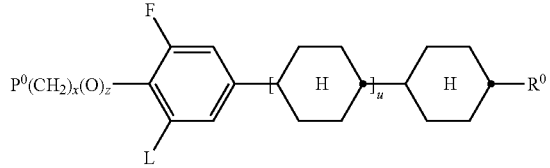
(R9)
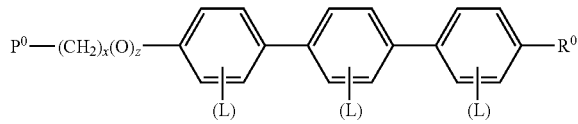
(R10)
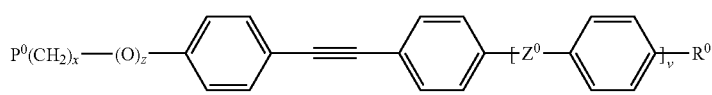
(R11)
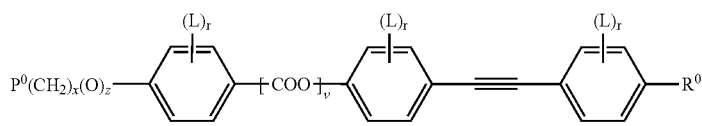
(R12)

-continued
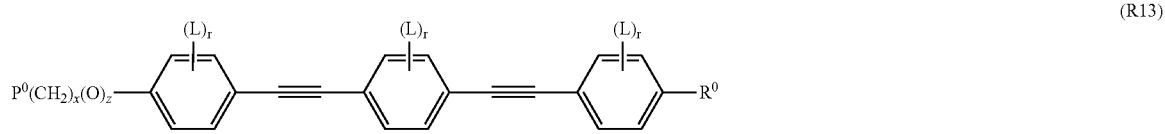
(R13)
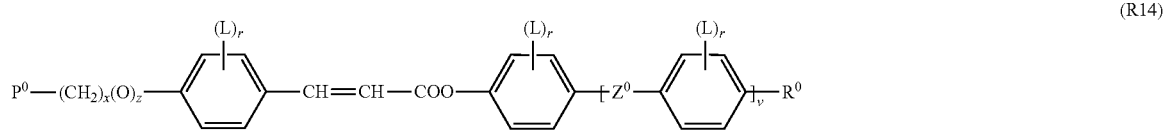
(R14)
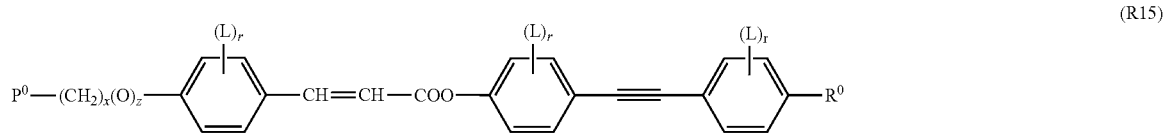
(R15)
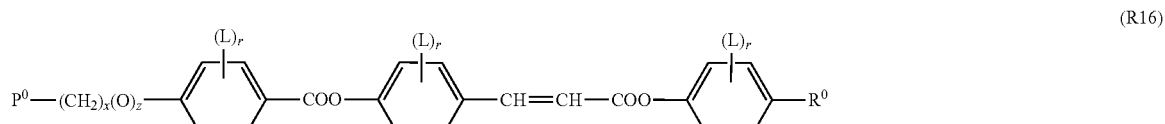
(R16)
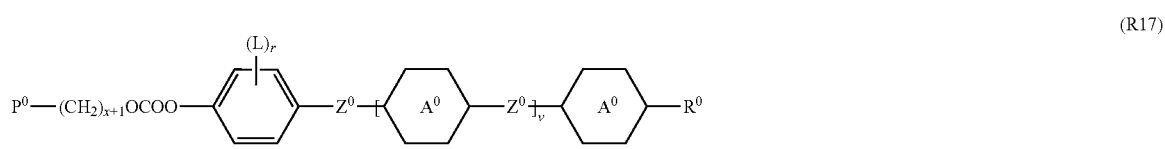
(R17)
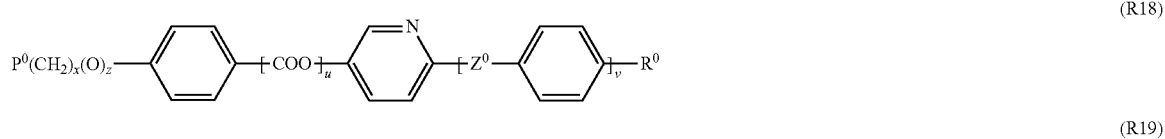
(R18)
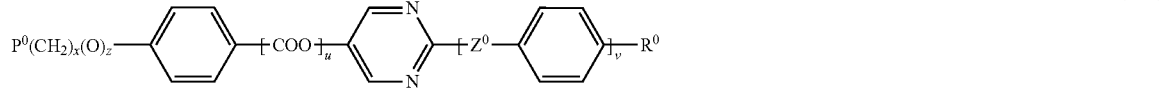
(R19)
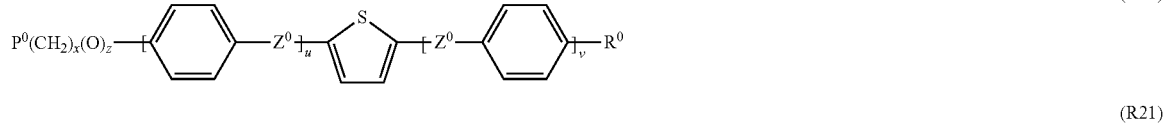
(R20)
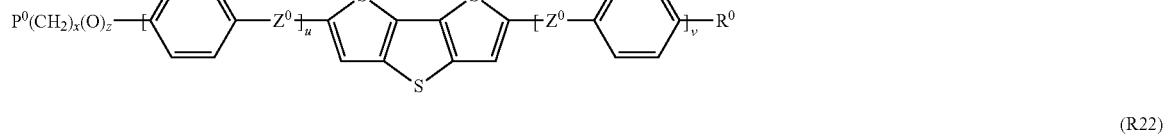
(R21)
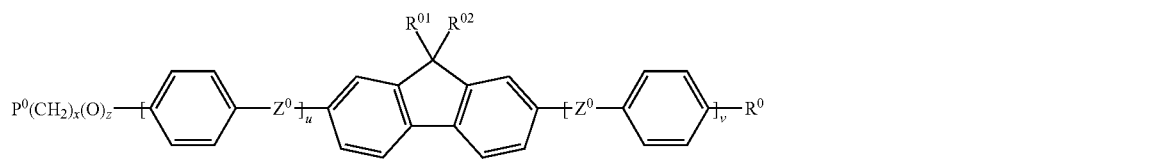
(R22)
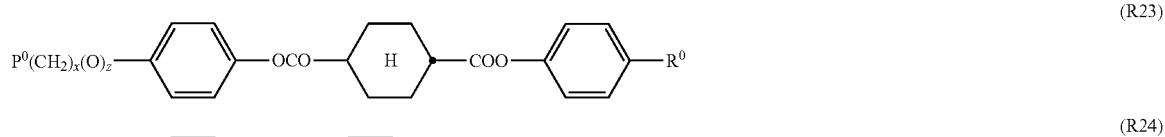
(R23)
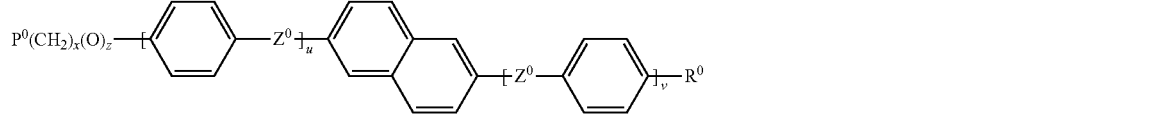
(R24)

-continued
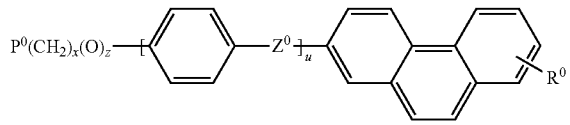
(R25)
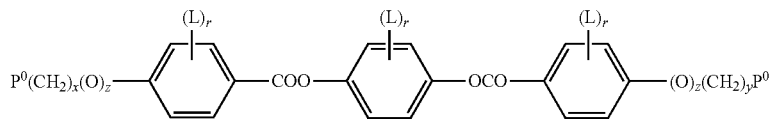
(R26)
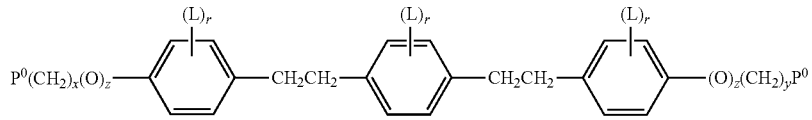
(R27)
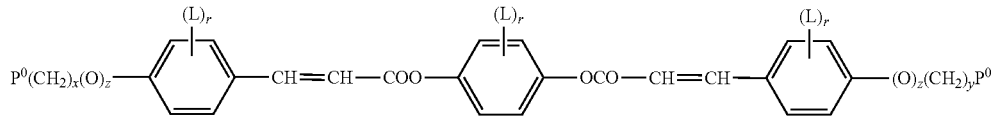
(R28)
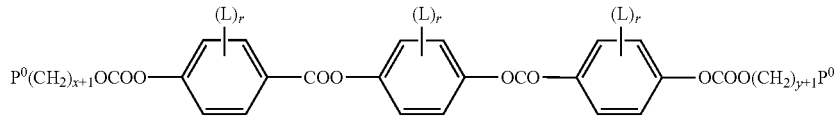
(R29)
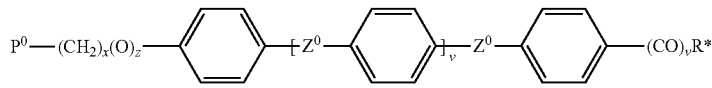
(R30)
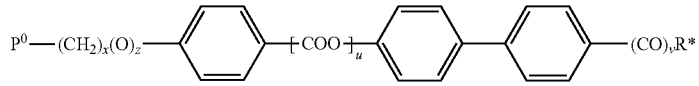
(R31)
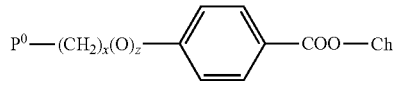
(R32)
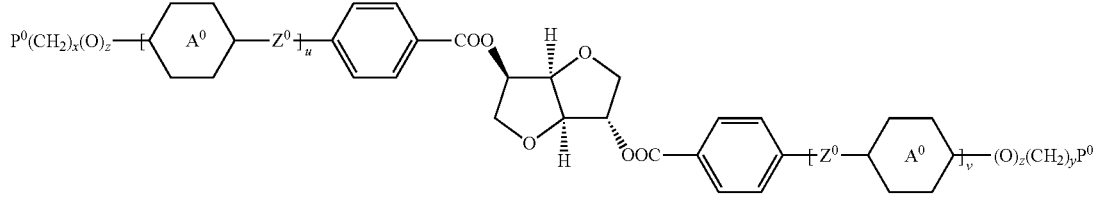
(R33)
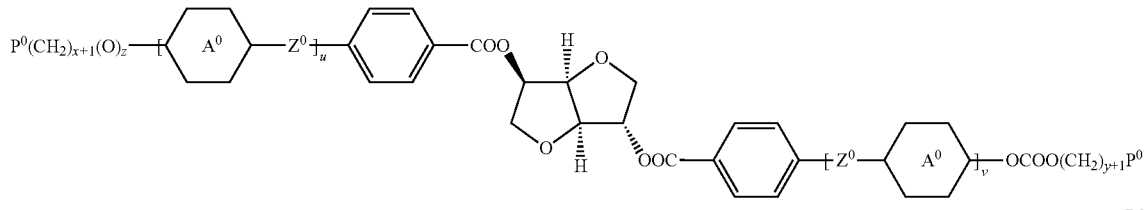
(R34)
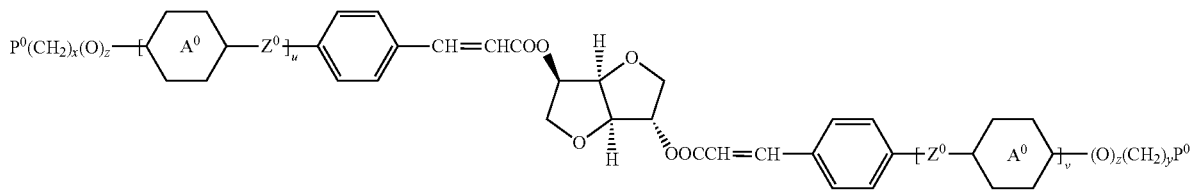
(R35)

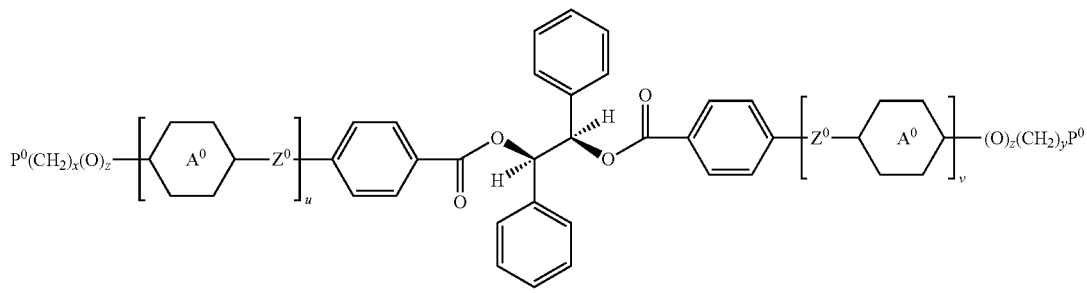

(R36)

wherein
P⁰ is, in case of multiple occurrence independently of one another, a polymerisable group, preferably an acryl, methacryl, oxetane, epoxy, vinyl, vinyloxy, propenyl ether or styrene group,
r is 0, 1, 2, 3 or 4,
x and y are independently of each other 0 or identical or different integers from 1 to 12,
z is 0 or 1, with z being 0 if the adjacent x or y is 0,
A⁰ is, in case of multiple occurrence independently of one another, 1,4-phenylene that is optionally substituted with 1, 2, 3 or 4 groups L, or trans-1,4-cyclohexylene,
u and v are independently of each other 0 or 1,
Z⁰ is, in case of multiple occurrence independently of one another, —COO—, —OCO—, —CH₂CH₂—, —C≡C—, —CH=CH—, —CH=CH—COO—, —OCO—CH=CH— or a single bond,
R⁰ is alkyl, alkoxy, thioalkyl, alkylcarbonyl, alkoxycarbonyl, alkylcarbonyloxy or alkoxycarbonyloxy with 1 or more, preferably 1 to 15 C atoms which is optionally fluorinated, or is Y⁰ or P—(CH₂)ᵧ—(O)₂—,
Y⁰ is F, Cl, CN, NO₂, OCH₃, OCN, SCN, SF₅, optionally fluorinated alkylcarbonyl, alkoxycarbonyl, alkylcarbonyloxy or alkoxycarbonyloxy with 1 to 4 C atoms, or mono- oligo- or polyfluorinated alkyl or alkoxy with 1 to 4 C atoms,
R⁰¹,⁰² are independently of each other H, R⁰ or Y⁰,
R* is a chiral alkyl or alkoxy group with 4 or more, preferably 4 to 12 C atoms, like 2-methylbutyl, 2-methyloctyl, 2-methylbutoxy or 2-methyloctoxy,
Ch is a chiral group selected from cholesteryl, estradiol, or terpenoid radicals like menthyl or citronellyl,
L is, in case of multiple occurrence independently of one another, H, F, Cl, CN or optionally halogenated alkyl, alkoxy, alkylcarbonyl, alkoxycarbonyl, alkylcarbonyloxy or alkoxycarbonyloxy with 1 to 5 C atoms,
and wherein the benzene rings can additionally be substituted with one or more identical or different groups L.

In addition to compounds of formula I, the polymerisable material may further comprise one or more polymerisable or unpolymerisable chiral compounds.

Suitable unpolymerisable chiral compounds are for example standard chiral dopants like R- or S-811, R- or S-1011, R- or S-2011, R- or S-3011, R- or S-4011, R- or S-5011, or CB 15 (all available from Merck KGaA, Darmstadt, Germany), sorbitols as described in WO 98/00428, hydrobenzoins as described in GB 2,328,207, chiral binaphthols as described in WO 02/94805, chiral binaphthol acetals as described in WO 02/34739, chiral TADDOLs as described in WO 02/06265, or chiral compounds having fluorinated linkage groups as described in WO 02/06196 or WO 02/06195. Suitable polymerisable chiral compounds are for example those listed above, or the polymerisable chiral material Paliocolor® LC756 (from BASF AG, Ludwigshafen, Germany).

The general preparation of polymer LC films according to this invention is known to the ordinary expert and described in the literature. Typically a polymerisable LC material is coated or otherwise applied onto a substrate where it aligns into uniform orientation, and polymerised in situ in its LC phase at a selected temperature for example by exposure to heat or actinic radiation, preferably by photo-polymerisation, very preferably by UV-photopolymerisation, to fix the alignment of the LC molecules. If necessary, uniform alignment can promoted by additional means like shearing or annealing the LC material, surface treatment of the substrate, or adding surfactants to the LC material.

As substrate for example glass or quartz sheets or plastic films can be used. It is also possible to put a second substrate on top of the coated material prior to and/or during and/or after polymerisation. The substrates can be removed after polymerisation or not. When using two substrates in case of curing by actinic radiation, at least one substrate has to be transmissive for the actinic radiation used for the polymerisation. Isotropic or birefringent substrates can be used. In case the substrate is not removed from the polymerised film after polymerisation, preferably isotropic substrates are used.

Suitable and preferred plastic substrates are for example films of polyester such as polyethyleneterephthalate (PET) or polyethylene-naphthalate (PEN), polyvinylalcohol (PVA), polycarbonate (PC) or triacetylcellulose (TAC), very preferably PET or TAC films. As birefringent substrates for example uniaxially stretched plastics film can be used. PET films are commercially available for example from DuPont Teijin Films under the trade name Melinex®.

The polymerisable material can be applied onto the substrate by conventional coating techniques like spin-coating or blade coating. It can also be applied to the substrate by conventional printing techniques which are known to the expert, like for example screen printing, offset printing, reel-to-reel printing, letter press printing, gravure printing, rotogravure printing, flexographic printing, intaglio printing, pad printing, heat-seal printing, ink-jet printing or printing by means of a stamp or printing plate.

It is also possible to dissolve the polymerisable material in a suitable solvent. This solution is then coated or printed onto the substrate, for example by spin-coating or printing or other known techniques, and the solvent is evaporated off before polymerisation. In many cases it is suitable to heat the mixture in order to facilitate the evaporation of the solvent. As solvents for example standard organic solvents can be used. The solvents can be selected for example from ketones such as acetone, methyl ethyl ketone, methyl propyl ketone or cyclohexanone; acetates such as methyl, ethyl or butyl acetate or methyl acetoacetate; alcohols such as methanol, ethanol or isopropyl alcohol; aromatic solvents such as toluene or xylene; halogenated hydrocarbons such as di- or trichloromethane; glycols or their esters such as PGMEA (propyl glycol monomethyl ether acetate), γ-butyrolactone, and the like. It is also possible to use binary, ternary or higher mixtures of the above solvents.

Initial alignment (e.g. planar alignment) of the polymerisable LC material can be achieved for example by rubbing treatment of the substrate, by shearing the material during or after coating, by annealing the material before polymerisation, by application of an alignment layer, by applying a magnetic or electric field to the coated material, or by the addition of surface-active compounds to the material. Reviews of alignment techniques are given for example by 1. Sage in "Thermotropic Liquid Crystals", edited by G. W. Gray, John Wiley & Sons, 1987, pages 75-77; and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Especially preferred is a polymerisable material comprising one or more surfactants that promote a specific surface alignment of the LC molecules. Suitable surfactants are described for example in J. Cognard, Mol. Cryst. Liq. Cryst. 78, Supplement 1, 1-77 (1981). Preferred aligning agents for planar alignment are for example non-ionic surfactants, preferably fluorocarbon surfactants such as the commercially available Fluorad FC-171® (from 3M Co.) or Zonyl FSN® (from DuPont), multiblock surfactants as described in GB 2 383 040 or polymerisable surfactants as described in EP 1 256 617.

It is also possible to apply an alignment layer onto the substrate and provide the polymerisable material onto this alignment layer. Suitable alignment layers are known in the art, like for example rubbed polyimide or alignment layers prepared by photoalignment as described in U.S. Pat. Nos. 5,602,661, 5,389,698 or 6,717,644.

It is also possible to induce or improve alignment by annealing the polymerisable LC material at elevated temperature, preferably at its polymerisation temperature, prior to polymerisation.

Polymerisation is achieved for example by exposing the polymerisable material to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation. As a source for actinic radiation for example a single UV lamp or a set of UV lamps can be used. When using a high lamp power the curing time can be reduced. Another possible source for actinic radiation is a laser, like for example a UV, IR or visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. For polymerising acrylate or methacrylate groups preferably a radical photoinitiator is used. For polymerising vinyl, epoxide or oxetane groups preferably a cationic photoinitiator is used. It is also possible to use a thermal polymerisation initiator that decomposes when heated to produce free radicals or ions that start the polymerisation. Typical radical photoinitiators are for example the commercially available Irgacure® or Darocure® (Ciba Geigy AG, Basel, Switzerland). A typical cationic photoinitiator is for example UVI 6974 (Union Carbide).

The polymerisable material may also comprise one or more stabilizers or inhibitors to prevent undesired spontaneous polymerisation, like for example the commercially available Irganox® (Ciba Geigy AG, Basel, Switzerland).

The curing time depends, inter alia, on the reactivity of the polymerisable material, the thickness of the coated layer, the type of polymerisation initiator and the power of the UV lamp. The curing time is preferably ≦5 minutes, very preferably ≦3 minutes, most preferably ≦1 minute. For mass production short curing times of ≦30 seconds are preferred.

Preferably polymerisation is carried out in an inert gas atmosphere like nitrogen or argon.

The polymerisable material may also comprise one or more dyes having an absorption maximum adjusted to the wavelength of the radiation used for polymerisation, in particular UV dyes like e.g. 4,4"-azoxy anisole or Tinuvin® dyes (from Ciba AG, Basel, Switzerland).

In another preferred embodiment the polymerisable material comprises one or more monoreactive polymerisable non-mesogenic compounds, preferably in an amount of 0 to 50%, very preferably 0 to 20%. Typical examples are alkylacrylates or alkylmethacrylates.

In another preferred embodiment the polymerisable material comprises one or more di- or multireactive polymerisable non-mesogenic compounds, preferably in an amount of 0 to 50%, very preferably 0 to 20%, alternatively or in addition to the di- or multireactive polymerisable mesogenic compounds. Typical examples of direactive non-mesogenic compounds are alkyldiacrylates or alkyldimethacrylates with alkyl groups of 1 to 20 C atoms. Typical examples of multireactive non-mesogenic compounds are trimethylpropanetrimethacrylate or pentaerythritoltetraacrylate.

It is also possible to add one or more chain transfer agents to the polymerisable material in order to modify the physical properties of the polymer film. Especially preferred are thiol compounds, for example monofunctional thiols like dodecane thiol or multifunctional thiols like trimethylpropane tri (3-mercaptopropionate). Very preferred are mesogenic or LC thiols as disclosed for example in WO 96/12209, WO 96/25470 or U.S. Pat. No. 6,420,001. By using chain transfer agents the length of the free polymer chains and/or the length of the polymer chains between two crosslinks in the polymer film can be controlled. When the amount of the chain transfer agent is increased, the polymer chain length in the polymer film decreases.

The polymerisable material may also comprise a polymeric binder or one or more monomers capable of forming a polymeric binder, and/or one or more dispersion auxiliaries. Suitable binders and dispersion auxiliaries are disclosed for example in WO 96/02597. Preferably, however, the polymerisable material does not contain a binder or dispersion auxiliary.

The polymerisable material can additionally comprise one or more additional components like for example catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes, pigments or nanoparticles.

The thickness of a polymer film according to the present invention is preferably from 0.3 to 5 microns, very preferably from 0.5 to 3 microns, most preferably from 0.7 to 1.5 microns. For use as alignment layer, thin films with a thickness of 0.05 to 1, preferably 0.1 to 0.4 microns are preferred.

The polymer film of the present invention can be used as retardation or compensation film for example in LCDs to improve the contrast and brightness at large viewing angles and reduce the chromaticity. It can be used outside the switchable LC cell of the LCD or between the substrates, usually glass substrates, forming the switchable LC cell and containing the switchable LC medium (incell application).

The polymer film of the present invention can also be used as alignment layer for LC materials. For example, it can be used in an LCD to induce or improve alignment of the switchable LC medium, or to align a subsequent layer of polymerisable LC material coated thereon. In this way, stacks of polymerised LC films can be prepared.

In particular, the chiral compounds, mixtures, polymers and polymer films according to the present invention can be used in reflective polarisers as disclosed in GB 2 315 072 or WO 97/35219, negative C plate retarders as disclosed in WO 01/20394 or WO 2004/013666, biaxial negative C plate retarders as disclosed in WO 2003/054111, alignment layers as disclosed in EP 1 376 163, birefringent markings or images for decorative or security use as disclosed in GB 2 315 760, WO 02/85642, EP 1 295 929 or EP 1 381 022.

The polymer film of the present invention can be used in conventional LC displays, for example displays with vertical alignment like the DAP (deformation of aligned phases), ECB (electrically controlled birefringence), CSH (colour super homeotropic), VA (vertically aligned), VAN or VAC (vertically aligned nematic or cholesteric), MVA (multi-domain vertically aligned) or PVA (patterned vertically aligned) mode; displays with bend or hybrid alignment like the OCB (optically compensated bend cell or optically compensated birefringence), R-OCB (reflective OCB), HAN (hybrid aligned nematic) or pi-cell (π-cell) mode; displays with twisted alignment like the TN (twisted nematic), HTN (highly twisted nematic), STN (super twisted nematic), AMD-TN (active matrix driven TN) mode; displays of the IPS (in plane switching) mode, or displays with switching in an optically isotropic phase or in the blue phase, as described for example in WO 02/93244.

Especially preferred are TN, STN, VA and IPS displays, in particular those of the active-matrix type. Further preferred are transflective displays.

In the foregoing and the following, all temperatures are given in degrees Celsius, and all percentages are by weight, unless stated otherwise. The following abbreviations are used to illustrate the LC phase behaviour: C, K=crystalline; N=nematic; S=smectic; N*, Ch=chiral nematic or cholesteric; I=isotropic. The numbers between these symbols indicate the phase transition temperatures in degree Celsius. Furthermore, mp is the melting point and cp is the clearing point (in ° C.).

Unless stated otherwise, the precentages of components of a polymerisable mixture as given above and below refer to the total amount of solids in the mixture polyrrierisable mixture, i.e. not including solvents.

The HTP of a chiral dopant in an LC host material is given as HTP=$(p*c)^{-1}$ (in $\mu m^{-1}$), wherein p is the pitch of the molecular helix (in µm) and c is the concentration (in wt. %) of the chiral compound in the host (a concentration of 1% by weight for example corresponds to c=0.01). Unless stated otherwise, specific HTP values given above and below relate to a dopant concentration of 1% in the LC host mixture MLC-6260 (Merck KGaA, Darmstadt, Germany) at 20° C.

The examples below shall illustrate the invention without limiting it. The corresponding S,S- or R,R-isomers of all binaphthyl compounds shown in the examples can also be prepared according or in analogy to the methods described.

EXAMPLE 1

Compound (1) is prepared according to reaction scheme 1.

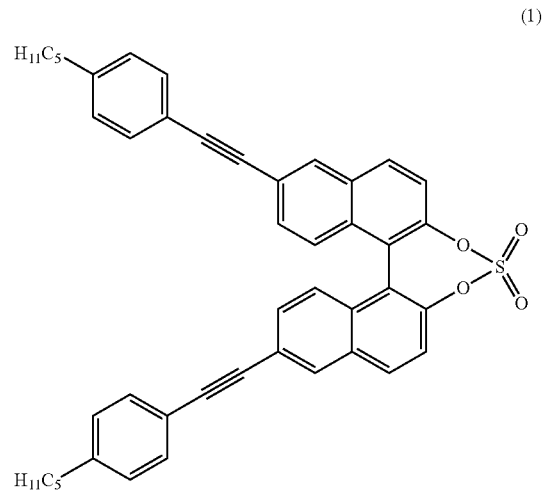

(1)

Preparation of S-(−)-9,14-Bis-(4-pentyl-phenylethynyl)-3,5-dioxa-4-thia-cyclohepta[2,1-a;3,4-a']dinaphthalene 4,4-dioxide (1)

Step 1: 6.6'-Dibromo-[1,1']binaphthalenyl-2,2'-diol

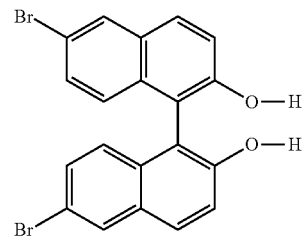

A solution of bromine (15.0 ml, 30.0 mmol) in dichloromethane (100 ml) is added dropwise to a solution of S-(−)-1,1'-Binaphthol (30.0 g, 10.5 mmol) in dichloromethane (200 ml) at −70° C. The reaction is allowed to warm to room temperature and stirred overnight. Excess bromine is destroyed by addition of aqueous sodium bisulphite. The aqueous layer is removed. The dichloromethane layer is washed with brine, water and dried over sodium sulphate. The solution is evaporated to dryness and the frothy residue is recrystallised from toluene and petrol to give a white solid (41.4 g, 89%). A mixture of 1:1 mono:di-brominated binaphthol is isolated. Since both intermediates are of interest, the mixture is taken through to the final reaction step before isolation of each. $^1$H NMR, GCMS and HPLC gave expected signals.

Step 2: S-(−)-9,14-Dibromo-3,5-dioxa-4-thia-cyclohepta[2,1-a;3,4-a']dinaphthalene 4,4-dioxide

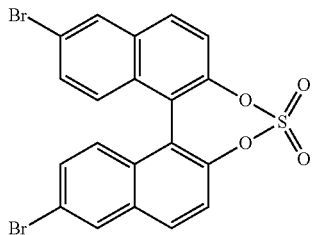

Sulphuryl chloride (7.8 ml, 57.5 mmol) is added to a solution of 6,6'-dibromo-[1,1']binaphthalenyl-2,2'-diol (20.0 g, 45.0 mmol) in pyridine (100 ml) at room temperature. After addition is completed, the solution is stirred at 90° C. for 30 minutes. The mixture is cooled to 50° C. and water (50 ml) is added. The mixture is added dropwise in to 20% hydrochloric acid solution (180 ml). A precipitate forms which is filtered off and put aside. Hydrochloric acid solution (20 ml, 20%) is added to the filtrate, the filtrate is warmed and filtered whilst hot. The combined precipitates are heated in industrial methylated spirit and filtered whilst hot. The resulting filtrate is evaporated to dryness to leave a red solid. The crude product mixture is purified by flash column chromatography using dichloromethane as eluant to give a yellowish oil. $^1$H NMR showed signals expected for a 1:1 mixture of mono and di-brominated product (10 g, 53%). This is used without further purification in step 3.

Step 3: S-(−)-9.14-Bis-(4-pentyl-phenylethynyl)-3,5-dioxa-4-thia-cyclohepta[2,1-a;3,4-a']dinaphthalene 4,4-dioxide

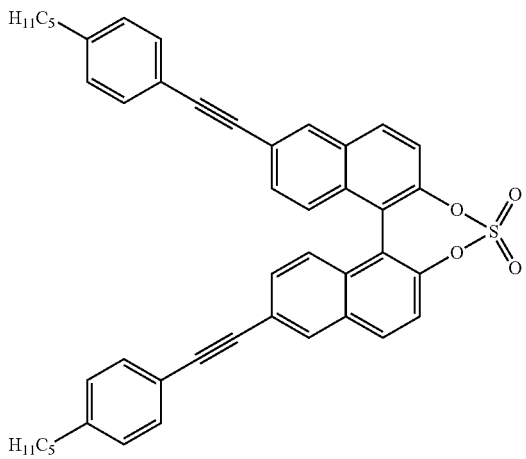

1-Ethynyl-4-pentylbenzene (3.4 g, 20.0 mmol) in tetrahydrofuran (20 ml) is added very slowly to a catalytic amount of PdCl$_2$(PPh$_3$)$_2$ (0.4 g, 0.56 mmol) a catalytic amount of copper (1) iodide and (9,14-dibromo-3,5-dioxa-4-thia-cyclohepta[2,1-a;3,4-a']dinaphthalene 4,4-dioxide (and the mono-brominated intermediate from step 2) (5.0 g, 9.9 mmol) in tetrahydrofuran (20 ml) at 70° C. The reaction is stirred for 16 hours, cooled to room temperature, diluted with dichloromethane and washed with water. The DCM layer is removed, dried over sodium sulphate and evaporated to dryness. The residue is purified by flash column chromatography to give the desired product as a white crystalline solid (2.1 g, 58%). $^1$H NMR gave expected signals.

The following phase transitions are observed by optical microscopy: K 153.5 I.

The extrapolated HTP is 52 (determined by the wedge cell method from a solution of 7.0 weight % of (1) in BL087, a commercially available nematic LC host mixture from Merck Chemicals Ltd, UK).

EXAMPLE 2

Compound (2) is prepared as follows:

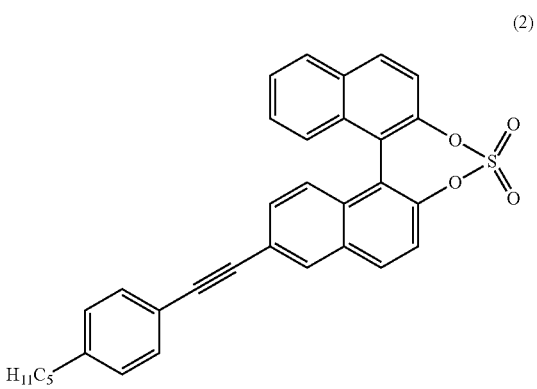

(2)

Evaporation of the appropriate fractions in step 3 of example 1 gives compound 2, S-(−)-9-(4-Pentyl-phenylethynyl)-3,5-dioxa-4-thia-cyclohepta[2,1-a;3,4-a']dinaphthalene 4,4-dioxide as a white powder (0.9 g).

The following phase transitions are observed by optical microscopy: K 76 I.

The extrapolated HTP is 45 (determined by the wedge cell method from a solution of 7.0 weight % of (2) in BL087, a commercially available nematic LC host mixture from Merck Chemicals Ltd, UK).

EXAMPLE 3

Compound (3) is prepared according to reaction scheme 6.

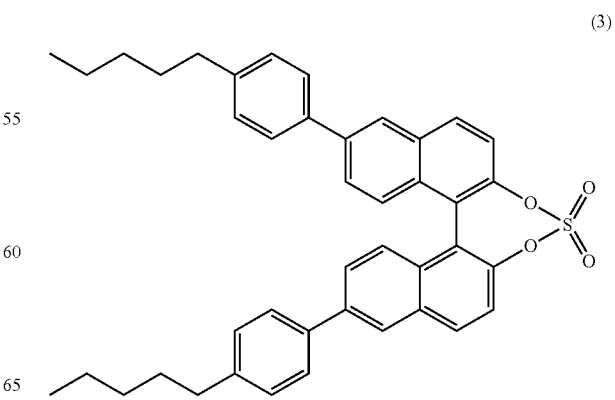

(3)

Preparation of S-(−)-9,14-Bis-(4-pentyl-phenyl)-3,5-dioxa-4-thia-cyclohepta[2,1-a;3,4-a']dinaphthalene 4,4-dioxide S-(−)-9,14-Dibromo-3,5-dioxa-4-thia-cyclohepta[2,1-a;3,4-a']dinaphthalene 4,4-dioxide (2.0 g, 3.95 mmol) is reacted with 4-pentylphenyl boronic acid (1.5 g, 8.0 mmol), a catalytic amount of tetrakis triphenylphoshine palladium (0), sodium carbonate (0.8 g, 8.0 mmol) and is stirred at 80° C. in a solution of tetrahydrofuran (50 ml) and water (10 ml) overnight. The mixture is allowed to cool, water and dichloromethane are added, the 2 layers are shaken, allowed to separate, the DCM layer is removed, washed with water, dried and evaporated to dryness. Purification using flash column chromatography gives a frothy solid (0.8 g). $^1$H NMR gives expected signals.

The following phase transition is observed by optical microscopy: K 75 I.

The extrapolated HTP is 37 (determined by the wedge cell method from a solution of 7.0 weight % of (2) in BL087, a commercially available nematic LC host mixture from Merck Chemicals Ltd, UK).

The invention claimed is:
1. A compound of formula I

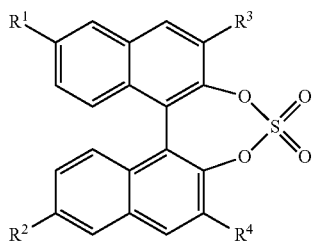

wherein
$R^{1-4}$ independently of each other denote H, F, Cl, Br, I, CN, NCS, SF$_5$, or straight-chain, branched or cyclic alkyl, aryl or heteroaryl having 1 to 30 C-atoms that is optionally mono- or polysubstituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote -(Z$^1$-A$^1$)$_m$-R$^5$ or P-Sp-,
$R^5$ has one of the meanings of $R^1$ that is different from -(Z$^1$-A$^1$)$_m$-R$^5$,
P is a polymerisable group,
Sp is a spacer group or a single bond,
$A^1$ is in case of multiple occurrence independently of one another an aromatic or alicyclic group, which optionally contains one or more hetero atoms selected from N, O and S, and is optionally mono- or polysubstituted by $R^1$,
$Z^1$ in case of multiple occurrence independently of one another denotes —O—, —S—, —CO—, —COO—, —OCO—, —S—CO—, —CO—S—, —O—COO—, —CO—NR$^0$—, —NR$^0$—CO—, —NR$^0$—CO—NR$^{00}$—, —NR$^0$—CO—O—, —O—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_4$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond,
$R^0$ and $R^{00}$ independently of each other denote H or alkyl with 1 to 12 C-atoms,
$Y^1$ and $Y^2$ independently of each other denote H, F, Cl or CN,
m is 0, 1, 2, 3 or 4,
wherein the binaphthyl group is optionally substituted in further positions by one or more identical or different groups $R^1$, and wherein the compound comprises at least one substituent $R^{1-4}$ that is different from H.

2. A compound according to claim 1, which comprises at least one group $R^{1-4}$ or $R^5$ that is P-Sp-.

3. A compound according to claim 1, wherein $R^1$ and/or $R^2$ or $R^3$ and/or $R^4$ denote P-Sp-.

4. A compound according to claim 1, wherein $R^1$ and/or $R^2$ or $R^3$ and/or $R^4$ denote -(Z$^1$-A$^1$)$_m$-R$^5$.

5. A compound according to claim 1, wherein -(Z$^1$-A$^1$)$_m$- is selected from the following formulae and their mirror images

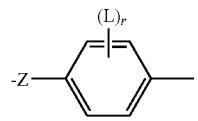

IIa

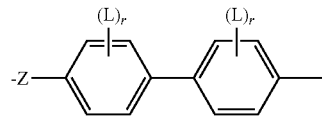

IIb

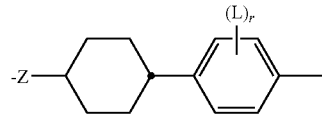

IIc

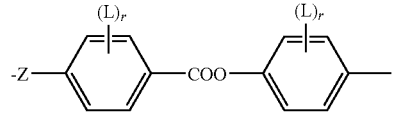

IId

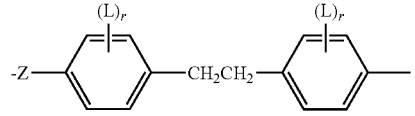

IIe

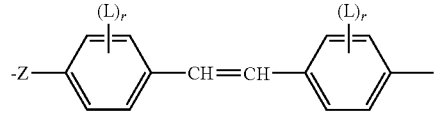

IIf

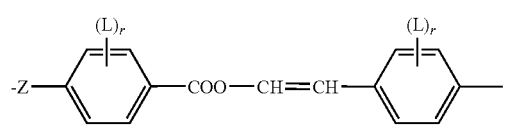

IIg

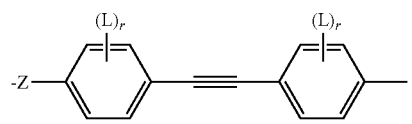

IIh

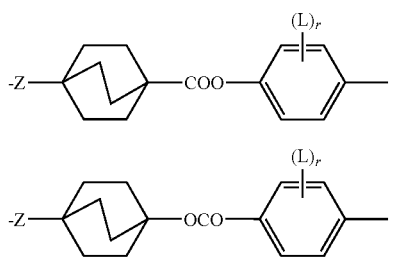
wherein L has one of the meanings of R¹ for the compound of formula I Z has one of the meanings of Z¹ for the compound of formula I and r is 0, 1, 2, 3 or 4.
6. A compound according to claim 1, which is one of the following formulae
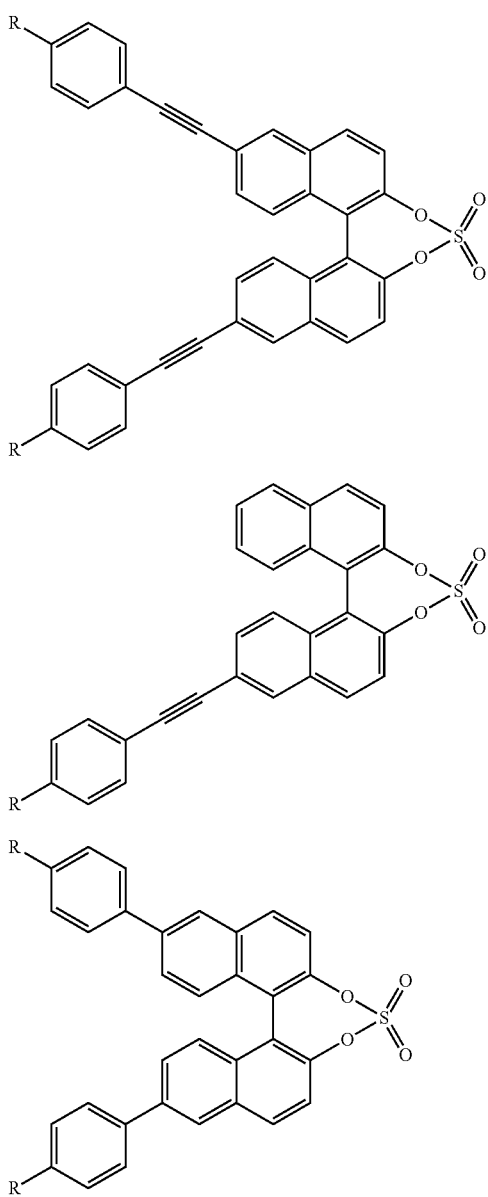
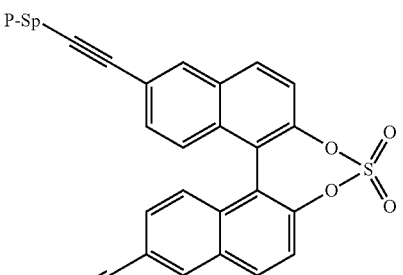
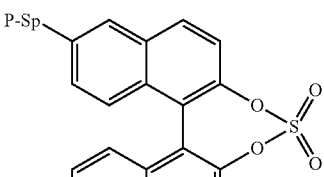
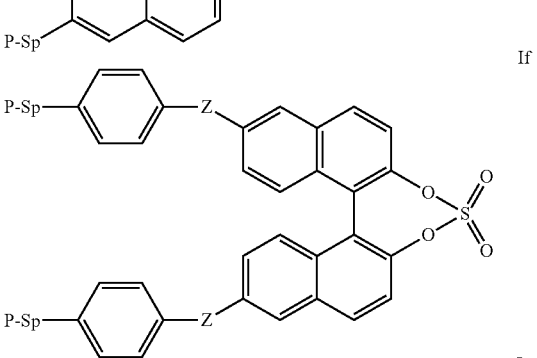
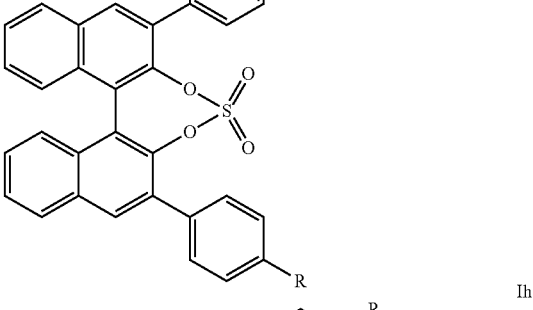
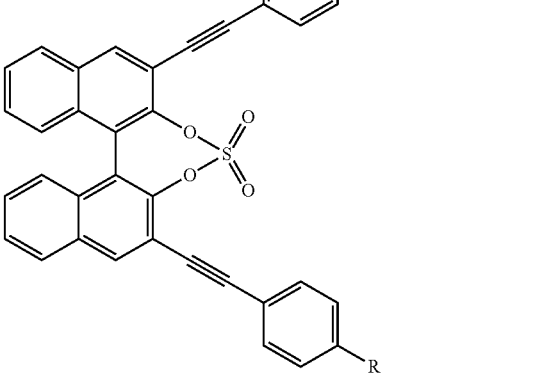

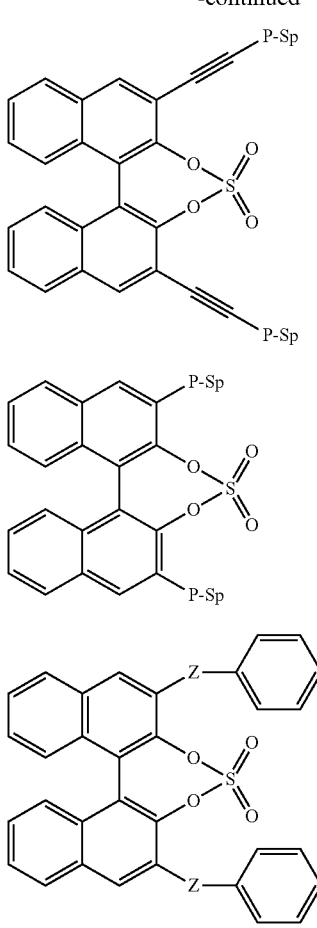

wherein R has one of the meanings of $R^1$ given for the compound of formula I P and Sp are as defined for the compound of formula I and Z has one of the meanings of $Z^1$ given for the compound of formula I.

7. A liquid crystal mixture, comprising at least one compound according to claim 1 and at least one further liquid crystalline compound.

8. A polymer or anisotropic polymer film obtained by polymerising a compound according to claim 1 or a mixture that comprises said compound and at least one further liquid crystalline compound in the liquid crystal phase and/or in an oriented state.

9. A product selected from the group consisting of electrooptical displays, LCDs, optical films, polarisers, compensators, beam splitters, reflective films, alignment layers, colour filters, holographic elements, hot stamping foils, coloured images, decorative and security markings, LC pigments, adhesives, cosmetics, diagnostics, non-linear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials, lasing devices, and chiral dopants, comprising a compound of formula I according to claim 1, or a liquid mixture that comprises at least one compound of formula I and at least one further liquid crystalline compound, or a polymer or anisotropic polymer film obtained by polymerising a compound of formula I or a mixture that comprises said compound and at least one further liquid crystalline compound in the liquid crystal phase and/or in an oriented state.

10. A liquid crystal display, colour filter, polariser, retardation film, alignment layer, authentification, verification or security marking, coloured image, object or document of value, comprising a compound of formula I , according to claim 1, or a liquid mixture that comprises at least one compound of formula I and at least one further liquid crystalline compound, or a polymer or anisotropic polymer film obtained by polymerising a compound of formula I or a mixture that comprises said compound and at least one further liquid crystalline compound in the liquid crystal phase and/or in an oriented state.

11. A method of preparing a compound according claim 1, comprising
  a) reacting binaphthol with bromine,
  b) reacting the intermediate 6,6'-dibromo-binaphthalenyl-2,2'-diol with sulphuryl chloride or another sulphuric acid derivative to form a dibromobinaphthtol sulphate intermediate, and
  c1) reacting the dibromobinaphthol sulphate intermediate with an aromatic or aliphatic acetylene compound in the presence of a base, and a catalytic amount of a copper salt and a palladium catalyst
  or
  c2) Grignard reaction of the dibromobinaphthol sulphate intermediate with a borate, followed by hydrolysis to give the boronic acid intermediate,
  d2) reaction of the boronic acid intermediate with $H_2O_2$ to give a phenol,
  e2) esterification of the phenol with an aliphatic or aromatic carboxylic acid derivative in the presence of a base,
  or
  c3) Grignard reaction of the dibromobinaphthol sulphate intermediate with a borate, followed by hydrolysis to give the boronic acid intermediate,
  d3) reaction of the boronic acid intermediate with $H_2O_2$ to give a phenol,
  e3) etherification of the phenol by means of an aliphatic or aromatic halogenid in the presence of a base,
  or
  c4) Grignard reaction of the dibromobinaphthol sulphate intermediate with a borate, followed by hydrolysis to give the boronic acid intermediate,
  d4) palladium C-C cross coupling of the boronic acid intermediate with an aliphatic or aromatic halogenid under Suzuki conditions,
  or
  c5) palladium C-C cross coupling of the dibromobinaphthol sulphate intermediate with an aliphatic or aromatic boronic acid under Suzuki conditions.

* * * * *

UNITED STATES PATENT AND TRADEMARK OFFICE
CERTIFICATE OF CORRECTION

PATENT NO. : 7,943,061 B2
APPLICATION NO. : 12/296598
DATED : May 17, 2011
INVENTOR(S) : Louise Diane Farrand et al.

Page 1 of 1

It is certified that error appears in the above-identified patent and that said Letters Patent is hereby corrected as shown below:

Title Page, (75) Inventors reads: "Louise Diane Farrand, Poole (GB); should read --Louise Diane Farrand, Poole, Dorset (GB)--.

Column 35, Line 15 reads: "of formula I Z has one of the meanings of $Z^1$ for the" should read --of formula I, Z has one of the meanings of $Z^1$ for the--.

Column 35, Line 16 reads: "compound of formula I and r is 0, 1, 2, 3, or 4." should read --compound of formula I, and r is 0, 1, 2, 3, or 4--.

Column 37, Line 39 reads: "compound of formula I P and Sp are as defined for the" should read --compound of formula I, P and Sp are as defined for the--.

Column 38, Line 13 reads: "value, comprising a compound of formula I , according to" should read --value, comprising a compound of formula I, according to--.

Column 38, Line 24 reads: "b) reacting the intermediate 6,6'-dibromo-binaphthalenyl-" should read --b) reacting the intermediate 6,6'-dibromo[1,1']-binaphthalenyl- --.

Column 38, Line 31 reads: "salt and a palladium catalyst" should read --salt and a palladium catalyst,--.

Signed and Sealed this
Twenty-third Day of August, 2011

David J. Kappos
*Director of the United States Patent and Trademark Office*